United States Patent
Sierks et al.

(10) Patent No.: US 9,512,212 B2
(45) Date of Patent: Dec. 6, 2016

(54) BISPECIFIC ANTIBODY FRAGMENTS FOR NEUROLOGICAL DISEASE PROTEINS AND METHODS OF USE

(71) Applicant: Arizona Board of Regents, a Body Corporate of the State of Arizona, Acting for and on Behalf of Arizona State University, Scottsdale, AZ (US)

(72) Inventors: Michael Sierks, Fort McDowell, AZ (US); Yong Shen, Bradenton, FL (US)

(73) Assignee: Arizona Board of Regents, a Body Corporate of the State of Arizona, Acting for and on Behalf of Arizona State University, Scottsdale, AZ (US)

(*) Notice: Subject to any disclaimer, the term of this patent is extended or adjusted under 35 U.S.C. 154(b) by 0 days.

(21) Appl. No.: 14/370,199

(22) PCT Filed: Jan. 10, 2013

(86) PCT No.: PCT/US2013/021032
§ 371 (c)(1),
(2) Date: Jul. 1, 2014

(87) PCT Pub. No.: WO2013/106572
PCT Pub. Date: Jul. 18, 2013

(65) Prior Publication Data
US 2014/0341907 A1    Nov. 20, 2014

Related U.S. Application Data

(60) Provisional application No. 61/585,539, filed on Jan. 11, 2012.

(51) Int. Cl.
G01N 33/541    (2006.01)
G01N 33/563    (2006.01)
(Continued)

(52) U.S. Cl.
CPC ............. *C07K 16/18* (2013.01); *C07K 16/283* (2013.01); *C07K 16/40* (2013.01); *C07K 16/42* (2013.01);
(Continued)

(58) Field of Classification Search
None
See application file for complete search history.

(56) References Cited

U.S. PATENT DOCUMENTS

2003/0059937 A1* 3/2003 Ruben .............. A61K 47/48561
435/345
2003/0073655 A1 4/2003 Chain
(Continued)

FOREIGN PATENT DOCUMENTS

GB    WO2009074583    *    6/2009    ............. C07K 16/18
WO    2004039962 A2    5/2004
(Continued)

OTHER PUBLICATIONS

Pisalyaput et al., Complement component C1q inhibits b-amyloid- and serum amyloid P-induced neurotoxicity via caspase- and calpain-independent mechanisms. Journal of Neurochemistry | 2008 | 104 | 696-707.*
(Continued)

*Primary Examiner* — Kimberly A. Ballard
*Assistant Examiner* — Aurora M Fontainhas
(74) *Attorney, Agent, or Firm* — Viksnins Harris & Padys PLLP

(57) ABSTRACT

The present invention relates to therapeutic agents comprising bispecific recombinant antibody fragments to selectively clear a protein associated with a neurological disease and methods of use of these therapeutic agents to treat neurological diseases.

17 Claims, 3 Drawing Sheets

(51) Int. Cl.
| | |
|---|---|
| G01N 33/577 | (2006.01) |
| C07K 16/46 | (2006.01) |
| C07K 16/18 | (2006.01) |
| C07K 16/28 | (2006.01) |
| C07K 16/40 | (2006.01) |
| C07K 16/42 | (2006.01) |
| A61K 39/00 | (2006.01) |

(52) U.S. Cl.
 CPC ..... A61K 2039/505 (2013.01); C07K 2317/31 (2013.01); C07K 2317/622 (2013.01); C07K 2317/626 (2013.01); C07K 2317/734 (2013.01); C07K 2317/92 (2013.01); C07K 2319/02 (2013.01); C07K 2319/21 (2013.01); C07K 2319/41 (2013.01)

(56) References Cited

U.S. PATENT DOCUMENTS

| | | | |
|---|---|---|---|
| 2004/0220388 A1* | 11/2004 | Mertens | C07K 16/00 530/388.8 |
| 2007/0020678 A1 | 1/2007 | Ault-Riche et al. | |
| 2009/0186027 A1 | 7/2009 | Solomon et al. | |
| 2010/0260668 A1 | 10/2010 | Ghayur et al. | |

FOREIGN PATENT DOCUMENTS

| | | |
|---|---|---|
| WO | WO2006014478 A1 | 2/2006 |
| WO | WO2006036291 A2 | 4/2006 |
| WO | WO2009004494 A2 | 1/2009 |
| WO | WO2009074583 A1 | 6/2009 |
| WO | WO2011031720 A1 | 3/2011 |

OTHER PUBLICATIONS

Boado et al., Fusion Antibody for Alzheimer's Disease with Bidirectional Transport Across the Blood—Brain Barrier and Aβ Fibril Disaggregation. Bioconjugate Chem., 2007, 18 (2), pp. 447-455.*
Patent Cooperation Treaty, International Searching Authority, Search Report and Written Opinion for PCT/US2013/021032, 14 pages, Jun. 3, 2013.
Akiyama et al., (2000). "Inflammation and Alzheimer's disease." Neurobiology of Aging 21: 383-421.
Arawaka et al., (2002). "The levels of mature glycosylated nicastrin are regulated and correlate with gamma-secretase processing of amyloid beta-precursor protein." J. Neurochem. 83: 1065-1071.
Bard et al., (2000). "Peripherally administered antibodies against amyloid beta-peptide enter the central nervous system and reduce pathology in a mouse of Alzheimer disease." Nat. Med. 6: 916-919.
Barkhordarian et al., (2006). "Isolating recombinant antibodies against specific protein morphologies using atomic force microscopy and phage display technologies." Protein Eng. Des. Sel. 19: 497-502.
Boder et al., (2000). "Directed evolution of antibody fragments with monovalent femtomolar antigen-binding affinity." PNAS USA 97: 10701-10705.
Borchelt et al., (1997). "Accelerated amyloid deposition in the brains of transgenic mice coexpressing mutant presenilin 1 and amyloid precursor proteins." Neuron 19: 939-945.
Busciglio et al., (2002). "Altered metabolism of the amyloid beta precursor protein is associated with mitochondrial dysfunction in Down's syndrome." Neuron 33: 677-688.
Cai et al., (2001). "BACE1 is the major beta-secretase for generation of Abeta peptides by neurons." Nat. Neurosci. 4: 233-234.
Calhoun et al., (1998). "Neuron loss in APP transgenic mice." Nature 395: 755-756.
Check, (2002). "Nerve inflammation halts trial for Alzheimer's drug." Nature 415: 462.
Chowdhury et al., (1999). "Improving antibody affinity by mimicking somatic hypermutation in vitro." Nat. Biotechnol. 17: 568-572.
Cotman et al., (1996). "Mechanisms of neuronal death in Alzheimer's disease." Brain Pathol. 6(4): 493-506.
Curnow, (1997). "Clinical experience with CD64-directed immunotherapy. An overview." Cancer Immunol Immunother 45: 210-215.
Daugherty et al., (2000). "Quantitative analysis of the effect of the mutation frequency on the affinity maturation of single chain Fv antibodies." PNAS USA 97: 2029-2034.
Emadi et al., (2007). "Isolation of a human single chain antibody fragment against oligomeric alpha-synuclein that inhibits aggregation and prevents alpha-synuclein-induced toxicity." J. Mol. Biol. 368: 1132-1144.
Emadi et al., (2004). "Inhibiting aggregation of alpha-synuclein with human single chain antibody fragments." Biochemistry 43: 2871-2878.
Esler et al., (2002). "Activity-dependent isolation of the presenilin-gamma -secretase complex reveals nicastrin and a gamma substrate." PNAS USA 99: 2720-2725.
Forman et al., (2004). "Neurodegenerative diseases: a decade of discoveries paves the way for therapeutic breakthroughs." Nat. Med. 10: 1055-1063.
Fukumoto et al., (2002). "Beta-secretase protein and activity are increased in the neocortex in Alzheimer disease." Arch. Neurol. 59: 1381-1389.
Goutte et al., (2002). "APH-1 is a multipass membrane protein essential for the Notch signaling pathway in Caenorhabditis elegans embryos." PNAS USA 99: 775-779.
Hock et al., (2003). "Antibodies against beta-amyloid slow cognitive decline in Alzheimer's disease." Neuron 38: 547-554.
Holliger et al., (1997). "Retargeting serum immunoglobulin with bispecific diabodies." Nat. Biotechnol. 15: 632-636.
Holsinger et al., (2002). "Increased expression of the amyloid precursor beta-secretase in Alzheimer's disease." Ann. Neurol. 51: 783-786.
Hutter-Paier et al., (2004). "The ACAT inhibitor CP-113,818 markedly reduces amyloid pathology in a mouse model of Alzheimer's disease." Neuron 44: 227-238.
Irving et al., (1996). "Affinity maturation of recombinant antibodies using E. coli mutator cells." Immunotechnology 2: 127-143.
Ishii et al., (1997). "Abeta1-40 but not Abeta1-42 levels in cortex correlate with apolipoprotein E epsilon4 allele dosage in sporadic Alzheimer's disease." Brain Res 748: 250-252.
Jackson et al., (1995). "In vitro antibody maturation. Improvement of a high affinity, neutralizing antibody against IL-1 beta." J. Immunol. 154: 3310-3319.
Janus et al., (2000). "A beta peptide immunization reduces behavioural impairment and plaques in a model of Alzheimer's disease." Nature 408: 979-982.
Jarrett et al., (1993). "The carboxy terminus of the beta amyloid protein is critical for the seeding of amyloid formation: implications for the pathogenesis of Alzheimer's disease." Biochemistry 32: 4693-4697.
Johnson et al., (1992). "Complement mRNA in the mammalian brain: responses to Alzheimer's disease and experimental brain lesioning." Neurobiology of Aging 13: 641-648.
Kayed et al., (2003). "Common structure of soluble amyloid oligomers implies common mechanism of pathogenesis." Science 300: 486-489.
Kim et al., (1983). "Long-term culture of human oligodendrocytes. Isolation, growth and identification." J. Neurol. Sci. 62: 295-301.
Kim et al., (1997). "Presenilins and Alzheimer's disease." Curr. Opin. Neurobiol. 7: 683-688.
Kimberly et al., (2002). "Complex N-linked glycosylated nicastrin associates with active gamma-secretase and undergoes tight cellular regulation." J. Biol. Chem. 277: 35113-35117.
Kirkitadze et al., (2002). "Paradigm shifts in Alzheimer's disease and other neurodegenerative disorders: the emerging role of oligomeric assemblies." J. Neurosci. Res. 69: 567-577.

(56) References Cited

OTHER PUBLICATIONS

Klein, (2002). "Abeta toxicity in Alzheimer's disease: globular oligomers (ADDLs) as new vaccine and drug targets." Neurochem. Int. 41: 345-352.

Konishi et al., (2003). "The temporal localization of frame-shift ubiquitin-B and amyloid precursor protein, and complement proteins in the brain of non-demented control patients with increasing Alzheimer's disease pathology." Neurosci. Lett. 348: 46-50.

Kontermann et al., (1997). "Complement recruitment using bispecific diabodies." Nat. Biotechnol. 15: 629-631.

Lamb et al., (1999). "Amyloid production and deposition in mutant amyloid precursor protein and presenilin-1 yeast artificial chromosome transgenic mice." Nat. Neurosci. 2: 695-697.

Lee et al., (2002). "Mammalian APH-1 interacts with presenilin and nicastrin and is required for intramembrane proteolysis of amyloid-beta precursor protein and Notch." J. Biol. Chem. 277: 45013-45019.

Leem et al., (2002). "Presenilin 1 is required for maturation and cell surface accumulation of nicastrin." J. Biol. Chem. 277: 19236-19240.

Li et al- (2004). "Amyloid beta peptide load is correlated with increased beta-secretase activity in sporadic Alzheimer's disease patients." Proc. Natl. Acad. Sci. USA 101: 3632-3637.

Liu et al., (2004). "Proteolytic antibody light chains alter beta-amyloid aggregation and prevent cytotoxicity." Biochemistry 43: 9999-10007.

Liu et al., (2004). "Residues 17-20 and 30-35 of beta-amyloid play critical roles in aggregation." J. Neurosci. Res. 75: 162-171.

Liu et al., (2005). "Trehalose differentially inhibits aggregation and neurotoxicity of beta-amyloid 40 and 42." Neurobiol. Dis. 20: 74-81.

Lue et al., (1996). "Characterization of glial cultures from rapid autopsies of Alzheimer's and control patients." Neurobiology of Aging 17: 421-429.

Luo et al., (2001). "Mice deficient in BACE1, the Alzheimer's beta-secretase, have normal phenotype and abolished beta-amyloid generation." Nat. Neurosci. 4: 231-232.

Matsuoka et al., (2001). "Inflammatory responses to amyloidosis in a transgenic mouse model of Alzheimer's disease." Am. J. Pathol. 158: 1345-1354.

McCall et al., (1999). "Isolation and characterization of an anti-CD16 single-chain Fv fragment and construction of an anti-HER2/neu/anti-CD16 bispecific scFv that triggers CD16-dependent tumor cytolysis." Mol. Immunol. 36: 433-445.

McLean et al., (1999). "Soluble pool of Abeta amyloid as a determinant of severity of neurodegeneration in Alzheimer's disease." Ann. Neurol. 46: 860-866.

Mullan et al., (1992). "A pathogenic mutation for probable Alzheimer's disease in the APP gene at the N-terminus of beta-amyloid." Nat. Genet. 1: 345-347.

Nannenga et al., (2008). "Anti-oligomeric single chain variable domain antibody differentially affects huntingtin and alpha-synuclein aggregates." FEBS Letters 582: 517-522.

Naslund et al., (2000). "Correlation between elevated levels of amyloid beta-peptide in the brain and cognitive decline." Jama 283: 1571-1577.

Nicoll et al., (2003). "Neuropathology of human Alzheimer disease after immunization with amyloid-beta peptide: a case report." Nat. Med. 9: 448-452.

Oddo et al., (2003). "Triple-transgenic model of Alzheimer's disease with plaques and tangles: intracellular Abeta and synaptic dysfunction." Neuron 39: 409-421.

Olsen et al., (2000). "Function-based isolation of novel enzymes from a large library." Nat. Biotechnol. 18: 1071-1074.

Orgogozo et al., (2003). "Subacute meningoencephalitis in a subset of patients with AD after Abeta42 immunization." Neurology 61: 46-54.

Orr-Weaver et al., (1983). "Yeast recombination: the association between double-strand gap repair and crossing-over." PNAS USA 80: 4417-4421.

O'Shannessy et al., (1992). "Immobilization chemistries suitable for use in the BIAcore surface plasmon resonance detector." Anal Biochem 205: 132-136.

Palop et al., (2003). "Neuronal depletion of calcium-dependent proteins in the dentate gyrus is tightly linked to Alzheimer's disease-related cognitive deficits." PNAS USA 100: 9572-9577.

Rangan et al., (2003). "Degradation of beta-amyloid by proteolytic antibody light chains." Biochemistry 42: 14328-14334.

Rogers et al., (1992). "Complement activation by beta-amyloid in Alzheimer disease." PNAS USA 89: 10016-10020.

Schenk, (2002). "Amyloid-beta immunotherapy for Alzheimer's disease: the end of the beginning." Nat. Rev. Neurosci. 3: 824-828.

Schenk et al., (1999). "Immunization with amyloid-beta attenuates Alzheimer-disease-like pathology in the PDAPP mouse." Nature 400: 173-177.

Schier et al., (1996). "Isolation of picomolar affinity anti-c-erbB-2 single-chain Fv by molecular evolution of the complementarity determining regions in the center of the antibody binding site." J. Mol. Biol. 263: 551-567.

Selkoe, (1999). "Translating cell biology into therapeutic advances in Alzheimer's disease." Nature 399: A23-A31.

Selkoe, (2001). "Alzheimer's disease: genes, proteins, and therapy." Physiol. Rev. 81: 741-766.

Seubert et al., (1993). "Secretion of beta-amyloid precursor protein cleaved at the amino terminus of the beta-amyloid peptide." Nature 361: 260-263.

Shen et al., (2003). "Yin and Yang: complement activation and regulation in Alzheimer's disease." Prog. Neurobiol. 70: 463-472.

Shen et al., (1997). "Neuronal expression of mRNAs for complement proteins of the classical pathway in Alzheimer brain." Brain Res. 769: 391-395.

Shiraishi et al., (2004). "PEN-2 enhances gamma-cleavage after presenilin heterodimer formation." J. Neurochem. 90: 1402-1413.

Sisodia, (1999). "Alzheimer's disease: perspectives for the new millennium." J. Clin. Invest. 104: 1169-1170.

Sisodia, (2002). "Biomedicine. A cargo receptor mystery APParently solved?" Science 295: 805-807.

Stalder et al., (1999). "Association of microglia with amyloid plaques in brains of APP23 transgenic mice." Am. J. Pathol. 154: 1673-1684.

Steiner et al., (2002). "PEN-2 is an integral component of the gamma-secretase complex required for coordinated expression of presenilin and nicastrin." J. Biol. Chem. 277: 39062-39065.

Stemmer, (1994). "Rapid evolution of a protein in vitro by DNA shuffling." Nature 370: 389-391.

Stine et al., (2003). "In vitro characterization of conditions for amyloid-beta peptide oligomerization and fibrillogenesis." J. Biol. Chem. 278: 11612-11622.

Webster et al., (1997). "Aggregation state-dependent activation of the classical complement pathway by the amyloid beta peptide." J. Neurochem. 69: 388-398.

Webster et al., (1997). "Molecular and cellular characterization of the membrane attack complex, C5b-9, in Alzheimer's disease." Neurobiology of Aging 18: 415-421.

Webster et al., (2000). "Complement component C1q modulates the phagocytosis of Abeta by microglia." Exp. Neurol. 161: 127-138.

Weggen et al., (2001). "A subset of NSAIDs lower amyloidogenic Abeta42 independently of cyclooxygenase activity." Nature 414: 212-216.

Wolfe et al., (1999). "Two transmembrane aspartates in presenilin-1 required for presenilin endoproteolysis and gamma-secretase activity." Nature 398: 513-517.

Wu et al., (1998). "Artificial antibodies for affinity chromatography of homologous proteins: application to blood clotting proteins." Biotechnol. Prog. 14: 496-499.

Wu et al., (1998). "Stepwise in vitro affinity maturation of Vitaxin, an alphav beta3-specific humanized mAb." PNAS USA 95: 6037-6042.

Yang et al., (2003). "Elevated beta-secretase expression and enzymatic activity detected in sporadic Alzheimer disease." Nat. Med. 9: 3-4.

(56) References Cited

OTHER PUBLICATIONS

Yoshiike et al., (2003). "Specific compositions of amyloid-beta peptides as the determinant of toxic beta-aggregation." J. Biol. Chem. 278: 23648-23655.

Younkin, (1998). "The role of a beta 42 in Alzheimer's disease." J. Physiol. (Paris) 92: 289-292.

Yu et al., (2000). "Nicastrin modulates presenilin-mediated notch/glp-1 signal transduction and betaAPP processing." Nature 407: 48-54.

Zameer et al., (2006). "Single chain Fv antibodies against the 25-35 Abeta fragment inhibit aggregation and toxicity of Abeta42." Biochemistry 45: 11532-11539.

Zameer et al., (2008). "Anti-oligomeric Abeta single-chain variable domain antibody blocks Abeta-induced toxicity against human neuroblastoma cells." J. Mol. Bio.I 384: 917-928.

Stains et al., (2007). "Molecules that target beta-amyloid." ChemMedChem 2(12): 1674-1692.

Boddapati et al., (2011). "Inhibiting beta-Secretase Activity in Alzheimer's Disease Cell Models with Single-Chain Antibodies Specifically Targeting APP." Journal of Molecular Biology 405(2): 436-447.

Hwang et al., (2008). "Highly specific inhibition of Clq globular-head binding to human IgG: A novel approach to control and regulate the classical complement pathway using an engineered single chain antibody variable fragment." Mol. Immunol. 45(9): 2570-2580.

Zhang et al., (2010). "Analyzing Conformation of Fusion Protein on Bivalent Single-Chain Antibody with (Gly4Ser)n." Bioinformatics and Biomedical Engineering 2010, 4th International Conference on IEEE, pp. 1-4.

Liu et al., (2004). "Single chain variable fragments against beta-amyloid (Abeta) can inhibit Abeta aggregation and prevent abeta-induced neurotoxicity." Biochemistry 43: 6959-6967.

Kasturirangan et al., (2010). "Engineered Proteolytic Nanobodies Reduce A beta Burden and Ameliorate A beta-Induced Cytotoxicity." Biochemistry 49(21): 4501-4508.

Kasturirangan et al., (2010). "Targeted Hydrolysis of Beta-Amyloid with Engineered Antibody Fragments." Current Alzheimer Research 7(3): 214-222.

Andra, et al., "Expression of APP in transgenic mice: a comparison of neuron-specific promoters", Neurobiology of Aging 17(2): 183-190 (1996).

Morgan, et al., "A beta peptide vaccination prevents memory loss in an animal model of Alzheimer's disease", Nature 408: 982-985 (2000).

Xia, et al., "FAD mutations in presenilin-1 or amyloid precursor protein decrease the efficacy of a gamma-secretase nhibitor: evidence for direct involvement of PS1 in the gamma-secretase cleavage complex", Neurobiol. Dis. 7: 673-681 (2000).

\* cited by examiner

Figure 7

H1V2 anti-AB40

MAEVQLVESGGGVVRPGGSLRLSCAASGFTFDDYGMSWVRQAPGKGLEWVSGINWNGGSTGYADSVKGRFTISRD
NAKNSLYLQMNSLRAEDTAVYYCARRRYALDYWGQGTLVTVSRGGGGSGGGGSGGGGSSELTQDPAVSVALGQTVR
ITCQGDSLRSYYASWYQQKPGQAPVLVIYGKNNRPSGIPDRFSGSSSGNTASLTITGAQAEDEADYYCNSRDSSGNHVV
FGGGTKLTVLG

D9 antiAb40 (also called H1v3)

MAEVQLVESGGGVVRPGGSLRLSCAASGFTFDDYGMSWVRQAPGKGLEWVSGINWNGGSTGYADSVKGRFTISRD
NAKNSLYLQMNSLRAEDTAVYYCARRRYALDYWGQGTLVTVSRGGGGSGGGGSGGGGSSELTQDPAVSVALGQTVR
ITCQGDSLRSYYASWYQQKPGQAPVLVIYGKNNRPSGIPDRFSGSSSGNTASLTITGAQAEDEADYYCNSSGGVMSVV
VFGGGTKLTLLG

C1 antiAb40

MAQVQLVQSGAEVKKTGSSVKVSCKASGYTFTYRYLHWVRQAPGQALEWMGWITPFNGNTNYAQKFQDRVTITRD
RSMSTAYMELSSLRSEDTAVYYCARQKTRLFSAIMPEWGQGTLVTVSRGGGGSGGGGSGGGGSSELTQDPAVSVALG
QTVRITCQGDSLRSYYASWYQQKPGQAPVLVIYGKNNRPSGIPDRFSGSSSGNTASLTITGAQAEDEADYYCNSRDSSG
NHVVFGGGTKLTVLG

BISPECIFIC ANTIBODY FRAGMENTS FOR NEUROLOGICAL DISEASE PROTEINS AND METHODS OF USE

RELATED APPLICATIONS

This application is a 371 National Stage Application of International Application Number PCT/US2013/021032, filed Jan. 10, 2013, which claims priority to U.S. Provisional Application No. 61/585,539 that was filed on Jan. 11, 2012, the contents of which are incorporated by reference herein.

SEQUENCE LISTING

The instant application contains a Sequence Listing which has been submitted in ASCII format via EFS-Web and is hereby incorporated by reference in its entirety. Said ASCII copy, created on Dec. 30, 2015, is named 17555.006US1_SL.txt and is 8,353 bytes in size.

BACKGROUND OF THE INVENTION

Alzheimer's disease (AD) is characterized by the presence of numerous neuritic plaques, neurofibrillary tangles, and neuronal loss. The plaques, mainly composed of β-amyloid (Aβ) peptide fragments, are derived from the processing of amyloid precursor protein (APP) by β- and γ-secretases. The presence of reactive microglia, astrocytes, and complement factors associated with the fibrillar Aβ plaques suggests the development of a local and chronic inflammatory response within the plaque area and is consistent with the hypothesis that complement activation contributes to this inflammatory process. In Aβ brains, C1q, the first component of the classical complement pathway that binds fibrillar Aβ and activates complement, has been shown to be associated with fibrillar Aβ plaques. Other complement proteins have also been detected in the plaque area, and their synthesis has been shown to occur within the AD brain.

Aggregation and deposition of amyloid β-protein (Aβ or beta amyloid) is considered to be a primary pathological event in Alzheimer's disease (AD). The longer 42-43 amino acid Aβ forms have been implicated in the formation of amyloid plaques, the aggregation state of the peptide is critical in determining its neurotoxicity. Many different forms of Aβ have been identified and characterized including fibrils, proto-fibrils, annular structures, globular structures, amorphous aggregates and various soluble oligomers. Numerous studies indicate that small oligomeric morphologies of Aβ are the primary toxic species in AD. These small oligomers are also called "low-n oligomers" (i.e., dimers, trimers, or tetramers).

Accordingly, there exists the need for new therapies and reagents for the treatment of Alzheimer's disease, in particular, therapies and reagents capable of effecting a therapeutic and diagnostic benefit at physiologic (e.g., non-toxic) doses.

SUMMARY OF THE INVENTION

The present invention relates to therapeutic agents comprising bispecific recombinant antibody fragments to selectively clear proteins associated with neurological diseases, and methods of use of these therapeutic agents to treat neurological disease.

Certain embodiments of the present invention provide a bispecific antibody fragment comprising (a) a first ligand that specifically recognizes a protein associated with a neurodegenerative disease, and (b) a second ligand that specifically activates a classical complement pathway component or directly activate microglial cells.

Certain embodiments of the present invention provide a bispecific antibody comprising (a) a first scFv that is an H1 scFv specific for β-amyloid, wherein the first scFv has an amino-terminus and a carboxy-terminus, and (b) a second scFv, that is an scFv specific for C1q, wherein the second scFv has an amino-terminus and a carboxy-terminus, and (c) a (Gly$_4$Ser)$_3$ peptide linker (SEQ ID NO: 1) operably linking the carboxy-terminus of the first scFv to the amino-terminus of the second scFv.

Certain embodiments of the present invention provide a nucleic acid encoding a bispecific antibody described above.

Certain embodiments of the present invention provide a therapeutic composition comprising a bispecific antibody described above, in combination with a physiologically-acceptable, non-toxic vehicle.

Certain embodiments of the present invention provide a method of clearing aggregated and soluble Aβ comprising administering the bispecific antibody described above.

BRIEF DESCRIPTION OF DRAWINGS

FIG. 7. Sequences for H1v2 anti-Ab40 (SEQ ID NO: 6), H1v3 anti-Ab40 (also called D9antiAb40) (SEQ ID NO: 7), and C1 antiAb40 (SEQ ID NO: 8). The first two sequences are different variants that bind better than the original H1 sequence. The C1antiAb40 scFv binds near the c-terminal of Aβ, C1. These sequences omit the PELB leader and the end NotI/His tags.

DETAILED DESCRIPTION OF THE INVENTION

Figures 1A, 1B:
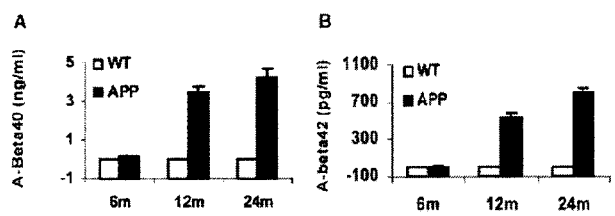
FIGS. 1A and 1B. Increased Aβ levels in APP mice with age. Brains from APP transgenic mice and wild type control mice at 6, 12 and 24 months old were homogenized and dissolved by formic acid. Aβ40 (panel A) and Aβ42 (panel 2B) concentrations were measured by Sandwich ELISA.

In certain embodiments, the present invention provides therapeutic agents comprising bispecific antibody fragments to selectively clear proteins associated with neurological diseases, and methods of use of these therapeutic agents to treat neurological diseases. Certain embodiments of the present invention provide a bispecific antibody fragment comprising (a) a first ligand that specifically recognizes a protein associated with a neurodegenerative disease, and (b) a second ligand that specifically activates a classical complement pathway component or directly activate microglial cells.

In certain embodiments, the bispecific antibody fragment further comprises a second bispecific antibody fragment to form a diabody construct. In certain embodiments, the first and second ligands are scFv fragments. In certain embodiments, the second ligand specifically binds to C1q (i.e., the first component of the classical complement response). In certain embodiments, the second ligand specifically binds to a receptor on a leukocyte, such as CD16 or CD64.

In certain embodiments, the bispecific antibody fragment treats a neurodegenerative disease such as Alzheimer's disease, Parkinson's disease, Lou Gehrig's disease, Huntington's disease, a prion disease or a spongiform encephalopathy. In certain embodiments, the neurodegenerative disease Alzheimer's disease and the first ligand that specifically recognizes Aβ (e.g., the first ligand is specific for soluble Aβ or is specific for aggregated Aβ). In certain embodiments, the bispecific antibody fragment further comprises a (Gly$_4$-Ser)$_3$ linker (SEQ ID NO: 1) operably linked between the first and second ligand. In certain embodiments, the bispecific antibody fragment further comprises a poly-His tail operably linked to either the first or second ligand.

Certain embodiments of the present invention provide a bispecific antibody comprising (a) a first scFv that is an H1 scFv specific for β-amyloid, wherein the first scFv has an amino-terminus and a carboxy-terminus, and (b) a second scFv that is an scFv specific for C1q, wherein the second scFv has an amino-terminus and a carboxy-terminus (c) a (Gly$_4$Ser)$_3$ peptide linker (SEQ ID NO: 1) operably linking the carboxy-terminus of the first scFv to the amino-terminus of the second scFv.

In certain embodiments, the bispecific antibody further comprises a gIII signal sequence operably linked to the amino-terminus of the first scFv. In certain embodiments, the bispecific antibody further comprises a c-myc tag operably linked to the carboxy-terminus of the second scFv. In certain embodiments, the bispecific antibody further comprises a (His)$_6$ tag (SEQ ID NO: 2) operably linked to the c-myc tag.

Certain embodiments of the present invention provide a nucleic acid encoding a bispecific antibody described above. In certain embodiments, the nucleic acid further comprises a promoter. Examples include, but are not limited to, a lac promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In certain embodiments, other control elements, such as enhancers and the like, will be of particular use. In certain embodiments, a gIII signal sequence is included at the 5' terminus. In certain embodiments, the nucleic acid further comprises a nucleic acid encoding a c-myc tag and a nucleic acid encoding a (His)$_6$ tag (SEQ ID NO: 2) that are positioned in-frame at the 3' terminal of the bispecific antibody. The gIII signal sequence directs the polypeptide into the periplasmic space, where it can fold correctly in a soluble form. The c-myc tag is used to analyze the expression level of the bispecific scFv, and (His)$_6$ tag (SEQ ID NO: 2) can be used to purify the bispecific scFv protein.

Certain embodiments of the present invention provide an expression cassette comprising the nucleic acid sequence described above and a promoter.

Certain embodiments of the present invention provide a vector comprising the expression cassette described above. In certain embodiments, the vector is a viral vector. In certain embodiments, the viral vector is an adenoviral, lentiviral, adeno-associated viral (AAV), poliovirus, HSV, or murine Maloney-based viral vector.

Certain embodiments of the present invention provide the vector or expression cassette described above.

Certain embodiments of the present invention provide a therapeutic composition comprising a bispecific antibody described above, in combination with a physiologically-acceptable, non-toxic vehicle.

Certain embodiments of the present invention provide a method of clearing aggregated and soluble Aβ comprising administering the bispecific antibody described above. In certain embodiments, the aggregated and soluble Aβ is in a cell, such as in brain tissue. In certain embodiments, the brain tissue is in a mammal, such as a human.

The present invention provides a method of suppressing the accumulation of a target protein (e.g., aggregated and soluble Aβ) in a cell by introducing a nucleic acid molecule described above into the cell in an amount sufficient to suppress accumulation of the target protein in the cell. In certain embodiments, the accumulation of target protein is suppressed by at least 10%. The accumulation of target protein is suppressed by at least 10%, 20%, 30%, 40%, 50%, 60%, 70%, 80%, 90% 95%, or 99%.

Neurological Diseases

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCAT, and SCA17), spinal and bulbar muscular atrophy (SBMA), dentatorubropallidoluysian atrophy (DRPLA). An example of a disabling neurological disorder that does not appear to result in atrophy is DYT1 dystonia. The gene of interest may encode a ligand for a chemokine involved in the migration of a cancer cell, or a chemokine receptor.

Alzheimer's Disease

Aβ, a major protein component (4 kDa) of the senile plaque, is generated from its precursor, APP, by enzymatic digestion involving β- and γ-secretase activities. The majority of Aβ fragments include Aβ$_{1-40}$ and Aβ$_{1-42}$. While Aβ$_{1-42}$ is believed to be the protein initially deposited in diffuse plaques as the seed molecule for amyloid fibril formation, subsequent deposition of $A\beta_{1-40}$ is more closely associated with the onset of clinical symptoms in late-onset AD, indicating that decreasing $A\beta$ concentration represents a potentially variable therapeutic or preventative approach. Two different approaches can be taken, one is to block $A\beta$ production, and a second is to clear $A\beta$ before it can cause damage. To block $A\beta$ production, the activity of the two different proteases that produce $A\beta$ from APP can be blocked: $\beta$-secretase cleaving APP to form the amino terminal of $A\beta$, and $\gamma$-secretase cleaving APP to form the carboxyl terminal of AP. While inhibition of either $\beta$- or $\gamma$-secretase activity is promising and is being very actively pursued by several labs and pharmaceutical companies, substantial hurdles are faced since the inhibitor must be delivered to numerous cellular locations to block cleavage of APP. The natural functions of these enzymes are relatively unknown so inhibition of the enzymes may result in other detrimental effects, and the inhibitor may block other protease activity as well causing unwanted side effects.

Cleavage of APP by $\beta$-secretase generates a ~100 kDa soluble $NH_2$-terminal fragment and a 12 kDa C-terminal stub of APP (C99), which can be further cleaved by a protease, $\gamma$-secretase. This cleavage yields two major species of $A\beta$, one ending at residue 40 ($A\beta_{40}$) and the other at residue 42 ($A\beta_{42}$). Endocytosis of APP is one route for generating $A\beta$; $A\beta$ can also be generated in the secretory pathway. Indeed, when APP was transfected into CHO cells and then subcellularly fractionalized, $A\beta_{42}$ was primarily detected in ER rich vesicles and $A\beta_{40}$ primarily in Golgi-rich vesicles.

Overexpression of $\beta$-secretase (BACE1) increases the amount of BACE1 cleavage products, C99 and C89. The role of BACE1 in $A\beta$ production in vitro might explain the higher production of $A\beta$ peptide in AD and the early onset of Swedish familial Alzheimer's disease. It has been demonstrated that BACE1 activity is elevated in sporadic AD brains. Studies using BACE knockout (KO) mice have demonstrated that BACE1 is the major $\beta$-secretase for the generation of $A\beta$ peptides and development of BACE1 inhibitors may be one effective approach to reduce $A\beta$ generation.

In addition, while $\gamma$-secretase also plays a critical role in generating $A\beta$, the second approach, clearing $A\beta$ from the brain, offers the advantage that it can avoid the problem of potentially interfering with other cell metabolic activities. Transgenic mice overexpressing mutant APP23 or both APP23 and PS1 variants were designed to develop $A\beta$ deposits similar to those found in AD patients. Therefore, these transgenic mice provide a suitable animal model to test various strategies to inhibit or clear $A\beta$ deposition. Immunization of such mice with aggregated $A\beta$ was shown to delay deposition of $A\beta$ and also to clear $A\beta$ deposits already present in the brain. Passive immunization of these same mice by periodic injection of antibodies generated against $A\beta$ was also shown to delay deposition of $A\beta$ and reduce $A\beta$ deposits that were already present. The clearance of $A\beta$ deposits from brain tissue in an ex vivo assay was correlated with Fc receptor mediated phagocytosis.

Behavioral studies of mice that were immunized against $A\beta$ also showed reduced memory loss and behavioral impairment. While these results are very encouraging, there are numerous potential difficulties in applying this strategy to humans, including the possibility that a strong immunization response may not be obtained or that immunization may exacerbate inflammation in brain tissue. There is considerable evidence that AD is an inflammatory disease and antibody mediated clearance by phagocytosis could exacerbate brain inflammation and damage. In human AD patients, active immunization against aggregated $A\beta$ decreased cognitive decline and reduced neuritic pathology providing clinical evidence for a role of $A\beta$ in AD pathology, however the study was suspended due to occurrence of aseptic meningoencephalitis in 6% of patients.

While the inflammatory response was not directly correlated with an antibody response, the full range of classical complement proteins are upregulated in AD brains, and $A\beta$ has been shown to bind C1q, the first components of the classical complement response. Therefore $A\beta$ can promote inflammation in the brain, and antibody mediated clearance of aggregated $A\beta$ can potentially further exacerbate this inflammation. While antibody mediated clearance represents a potentially powerful strategy for controlling $A\beta$ deposition, complement activation must be carefully regulated in AD brains, stimulated enough to provide clearance of pathogens or neurotoxic aggregates and to promote healing of neurons, but not too much that inflammation causes cognitive damage (Shen and Meri 2003).

Monoclonal antibodies to $A\beta$ have been previously isolated and shown to initiate clearance of aggregated $A\beta$, however there are several significant advantages to using the scFv antibody fragments proposed here including: 1) the scFv antibodies are derived from human cell lines and can be used for in vivo analysis and eventual treatment with less risk of an immunogenic response; 2) the scFv antibodies are much smaller than monoclonals, potentially facilitating transport across the BBB; 3) peptide sequences targeting transport across the BBB can be added to the recombinant antibody constructs to further favor biodistribution to the brain; 4) the diabody constructs can be readily modified to clear tau, prions or other potential neurodegenerative targets, and perhaps most importantly 5) combinations of antigenic targets and clearance mechanisms can be utilized to control inflammation.

To increase microglial clearance of AP, the inventors have developed an innovative approach for treating AD by using bispecific recombinant antibody fragments (diabodies) that are specifically engineered to address the critical inflammation problem currently confronting $A\beta$ clearance as a therapeutic strategy. The bispecific antibodies will contain two different binding activities, the first will selectively target different morphologies and forms of $A\beta$, while the second binding activity will either activate different components of the classical complement pathway or directly activate microglial cells to more selectively control the inflammatory response necessary for phagocytosis of $A\beta$. The diabodies contain scFv fragments targeted toward either soluble or fibrillar $A\beta$ in combination with scFv fragments that initiate different components of the clearance mechanisms.

$A\beta$ accumulation has been strongly correlated with AD, therefore inhibiting AP accumulation represents a promising therapeutic strategy. The $A\beta$ immunization trials in humans provide powerful evidence that clearance of $A\beta$ can be a viable therapeutic approach for treating AD providing the inflammatory response can be controlled. Inflammatory responses in AD brains that are lacking in healthy brains have been previously identified (Akiyama et al. 2000). While the inflammatory response was not directly correlated with an antibody response, the full range of classical complement proteins are upregulated in AD brains (Akiyama et al. 2000), and $A\beta$ has been shown to bind C1q, which is the first component of the classical complement response. Therefore $A\beta$ can promote inflammation in the brain, and antibody mediated clearance of aggregated Aβ can potentially further exacerbate this inflammation. Since a delicate balance already exists in the brain between healthy clearance and destructive inflammation, a therapeutic antibody mediated clearance strategy of Aβ must maintain this balance, as evidenced by complications observed in the human immunization trials (Check 2002).

Other Neurodegenerative Diseases

Beyond the tremendous potential therapeutic value for AD, the antibody constructs developed here represent a suitable paradigm for treating other neurological diseases such as Parkinson's Disease, Lou Gehrig's Disease, Huntington's Disease and spongiform encephalopathies. The antibody constructs are designed from separate and easily substituted functionalities, so the constructs can be readily modified for other applications. For example, prions can be targeted instead of Aβ by exchanging a prion specific scFv domain for the AP domain. Instead of complement activation, a specific protease activity can be activated by swapping the complement activating scFv with a proteolytic scFv.

Antibodies and Antibody Fragments

The present invention provides a purified bi-specific ligand that binds specifically to a protein associated with a neurodegenerative disease and binds to a component of cell clearance mechanisms. As used herein, the term "antibody" includes scFv, humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

As used herein, the term "antibody" includes a single-chain variable fragment (scFv or "nanobody"), humanized, fully human or chimeric antibodies, single-chain antibodies, diabodies, and antigen-binding fragments of antibodies (e.g., Fab fragments). A scFv is a fusion protein of the variable region of the heavy ($V_H$) and light chains ($V_L$) of an immunoglobulin that is connected by means of a linker peptide. The linker is usually short, about 10-25 amino acids in length. If flexibility is important, the linker will contain a significant number of glycines. If solubility is important, serines or theonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). Holliger et al., "Diabodies: small bivalent and bispecific antibody fragments," PNAS, July 1993, 90:6444-6448. Bivalency allows antibodies to bind to multimeric antigens with high avidity, and bispecificity allows the crosslinking of two antigens.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

Polyclonal and monoclonal antibodies can be prepared by methods known to those skilled in the art.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

The antibodies of the present invention also include antibodies which comprise complementarity-determining regions (CDRs), or regions functionally equivalent to CDRs. The term "functionally equivalent" refers to comprising amino acid sequences similar to the amino acid sequences of CDRs of any of the monoclonal antibodies isolated in the Examples. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as "framework," and their amino acid sequences are highly conserved. The CDRs can be transplanted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and preferably within 35%, and still more preferably within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$—$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')$_2$ fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as E. coli, and then allowed to form F(ab')$_2$ fragments by chemical crosslinking (Carter et al., Bio/Technology 10:163-167 (1992)). In an alternative method, F(ab')$_2$ fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133,988).

Nucleic Acid Molecules Encoding Antibodies

The present invention further provides nucleic acid sequences that encode the antibodies described above.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucl. Acids Res., 19:508 (1991); Ohtsuka et al., JBC, 260:2605 (1985); Rossolini et al., Mol. Cell. Probes, 8:91 (1994). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide"

may also be used interchangeably with gene, cDNA, DNA and RNA encoded by a gene.

The terms "protein," "peptide" and "polypeptide" are used interchangeably herein.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., *Mol. Biotech.*, 3:225 (1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position+1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (L e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller, CABIOS, 4:11 (1988); the local homology algorithm of Smith et al., Adv. Appl. Math., 2:482 (1981); the homology alignment algorithm of Needleman and Wunsch, J M B, 48:443 (1970); the search-for-similarity-method of Pearson and Lipman, Proc. Natl. Acad. Sci. USA, 85:2444 (1988); the algorithm of Karlin and Altschul, Proc. Natl. Acad. Sci. USA, 87:2264 (1990), modified as in Karlin and Altschul, Proc. Natl. Acad. Sci. USA, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988); Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994). The ALIGN program is based on the algorithm of Myers and Miller, supra. The BLAST programs of Altschul et al., JMB, 215: 403 (1990); Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm-.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., Nucleic Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98°/or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, New York (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

Formulations and Methods of Administration

For in vivo use, a therapeutic agent as described herein is generally incorporated into a pharmaceutical composition prior to administration. Within such compositions, one or more therapeutic compounds as described herein are present as active ingredient(s) (i.e., are present at levels sufficient to provide a statistically significant effect on the symptoms of cystic fibrosis, as measured using a representative assay). A pharmaceutical composition comprises one or more such compounds in combination with any pharmaceutically acceptable carrier(s) known to those skilled in the art to be suitable for the particular mode of administration. In addition, other pharmaceutically active ingredients (including other therapeutic agents) may, but need not, be present within the composition.

The term "therapeutically effective amount," in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat," "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

In certain embodiments, the present therapeutic agent may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

EXAMPLE 1

Transgenic mice have been developed that overexpress a mutant form of APP and develop neuropathological A$\beta$ plaques, show delayed deposition and even clearance of these plaques when immunized with A$\beta$. These results were extended to show that the same protection against A$\beta$ deposition could also be achieved by passive immunization where antibodies raised against A$\beta$ were periodically injected into mice (Bard et al. 2000). These studies raise the possibility that a carefully designed passive immunization approach can be used to clear Aβ in humans while controlling the delicate balance between clearance and inflammation. In order to understand how antibody mediated phagocytosis can be more effectively employed for the treatment of AD, below is a brief outline of a few of the critical components of the antibody mediated complement response system.

The complement system consists of over 20 different proteins that interact in a highly orchestrated series of enzymatic reactions which generate products that facilitate and amplify antigen clearance. The complement system can be activated by two different pathways, the classical or alternative pathways, both of which end up activating the same complexes. The classical pathway is initiated by antibody binding while the alternative pathway is generally initiated by foreign cell-surface components. The classical pathway is therefore the pathway of interest in the antibody mediated clearance of Aβ. The classical pathway is initiated by the formation of an antibody-antigen complex. Certain antibodies including IgM, IgG1, IgG2 and IgG3 are capable of activating the classical complement response upon antigen binding. When these antibodies bind their target antigen, the resulting complex induces a conformational change in the antibody Fc region. The conformational change in the Fc region exposes a binding site for the first component of the classical complement system, the macromolecular protein complex C1. C1 exists in serum as a complex containing one C1q molecule and two molecules each of C1r and C1s. Two C1-antibody interactions are generally required to form a stable complex. Since IgG has only one binding site for C1q, two IgG molecules bound on the antigenic surface within a distance of 30-40 nm are required for complement activation. IgM however can adapt a pentameric structure when bound to antigen and therefore a single molecule of IgM can stably bind C1 and initiate a complement response. In order to phagocytose either soluble or aggregated Aβ deposits, the antibodies must bind to the surface exposing the C1q binding site on the Fc portion of the antibody. Two C1q binding sites must be located in close enough proximity to form a stable antibody-C1 complex, which in turn initiates the complement response cascade ending with C3b and C5b bound to the antigenic surface. Phagocytic cells then bind C3b through CR1 receptors initiating phagocytosis and also forming C3bi, which in turn binds CR3 receptors further promoting phagocytosis.

Monoclonal antibody preparations may have difficulty in clearing Aβ, particularly soluble Aβ, since formation of a stable antibody C1 complex requires two adjacent Fc sites. Bispecific recombinant antibodies are made to both soluble and aggregated Aβ, which can activate antibody clearance through different mechanisms. The inventors have developed scFv fragments directed toward different components of the complement response cascade. One scFv fragment binds C1q in a manner that initiates clearance. A diabody construct containing an scFv binding hen egg lysozyme (HEL) and the scFv binding C1 q was shown to promote phagocytosis of red blood cells coated with HEL. A second scFv fragment binds serum Ig, binding both IgM and IgG. Diabody constructs containing an scFv targeting HEL along with the scFv binding serum Ig also promoted phagocytosis of red blood cells coated with HEL. In addition, scFvs binding different receptors that activate inflammatory or phagocytic responses in leukocytes (anti-CD16; and anti-CD64) are available to induce a response with the functionally related microglial cells. Further, new scFvs that directly activate microglial cells are isolated. Since ex vivo assays are predictive of in vivo clearance of Aβ deposits in mice (Bard et al. 2000), the ex vivo assay is used as a method to screen various combinations of bispecific antibodies targeting different morphologies of Aβ and activating different clearance mechanisms.

Generation of APP23/C1q$^{-/-}$ Mice.

Alzheimer-mouse model, APP23, overproduce Aβ and develop significant amyloid deposits. Brain homogenates from APP23 mice by ELISAs and immunoprecipitation blotting for Aβ levels were analyzed. Increased Aβ levels were observed in APP mice with age using a Sandwich ELISA (FIGS. 1A and 1B). Further, Aβ40 and Aβ42 were visualized by using a urea SDS/PAGE gel. Briefly, mouse brain homogenates were dissolved in formic acid buffer and immunoprecipitated with rabbit anti-Aβ polyclonal antibody and sample was separated on a 12% Urea gel. Aβ40 and Aβ42 were detected by the 6E10 antibody. APP23 mice were crossed with mice depleted of C1q (C1 q$^{-/-}$) to generate APP23/C1q$^{-/-}$ mice.

Construction of Aβ C1q Diabody.

In order to develop a therapeutic to clear Aβ in vivo, scFv fragments that bind both soluble and fibrillar Aβ are combined with scFv fragments that activate different components of the complement cascade or that bind to different receptors on leukocytes or that directly activate microglial cells. Each scFv consists of a light chain and heavy chain fragment connected with a short linker sequence into a single peptide. In certain embodiments, diabodies are constructed by genetically linking two scFvs in series using a long flexible (Gly$_4$-Ser)$_3$ linker (SEQ ID NO: 1). In certain embodiments, the diabodies are designed to also contain a poly-His tail to facilitate purification using metal ion affinity chromatography.

Two scFv diabody clones that have already been shown to activate the complement response and clear their target compounds through phagocytosis have been obtained, one binds serum immunoglobulin and the other complement component C1q. The inventors constructed a H1v2-C1q diabody and have purified fully functional bispecific diabody protein. In other embodiments, diabody molecules specific for Aβ42, oligomeric and fibrillar Aβ are constructed (Example 2). In addition, scFvs that bind to CD16 and CD64, both of which activate clearance by phagocytic cells, are available, and both have proven to be effective as bispecific diabody constructs for targeting and killing tumor cells (Curnow 1997; McCall et al. 1999).

Figure 2:
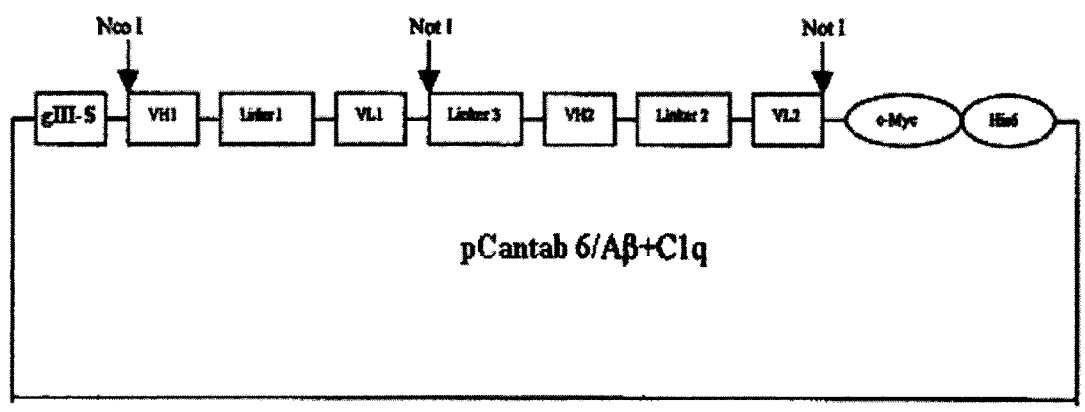
FIG. 2. Schematic diagram showing diabody s gene construct (pCantab6/Aβ+C1q). pelB, signal peptide sequence of bacterial pectatelyase; c-myc, a sequence encoding an epitope recognized by the monoclonal antibody 9E10; His6, a sequence encoding six C-terminal histidine residues (SEQ ID NO: 2).

To generate a diabody containing scFvs to both β-amyloid and C1q, the inventors cloned the H1v2 scFv gene isolated against β-amyloid downstream to the scFv against C1q. A (Gly$_4$Ser)$_3$ peptide linker (SEQ ID NO: 1) was used to connect the carboxyl terminus of H1v2 with the amino terminus of the anti-C1q scFv. The resulting diabody has two domains, linked by a (Gly$_4$Ser)$_3$ peptide linker (SEQ ID NO: 1) (FIG. 2). The diabody gene is under control of lac promoter and is in frame with gIII signal sequence at the 5' terminal. To facilitate detection and recovery of the diabody, a c-myc tag and a (His)$_6$ tag (SEQ ID NO: 2) were inserted in frame at the 3' terminal of the bispecific scFv. The gIII signal sequence directs the polypeptide into the periplasmic space, where it can fold correctly in a soluble form. The c-myc tag is used to analyze the expression level of the bispecific scFv, and (His)$_6$ tag (SEQ ID NO: 2) can be used to purified the bispecific scFv protein.

Protein Purification.

After induction with IPTG, the soluble periplasmic content of the *E. coli* culture was purified by IMAC (immobilized metal affinity chromatography). SDS-PAGE analysis of peak fractions eluted using 50 mM imidazole indicated one fraction containing a single strong band of size 60 kDa, the size expected for the diabody. Western blot analysis of this sample using a secondary antibody to the myc-tag site indicated a single reactive band, with the expected size of 60 kD.

Antigen Binding Activity of the Purified Bispecific Antibody Fragment.

Figure 3:
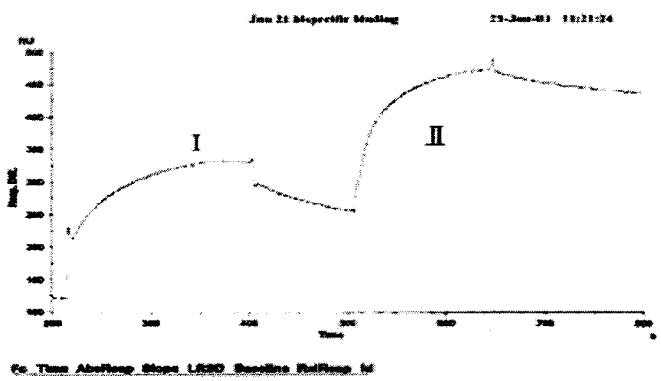
FIG. 3. BIAcore binding analysis of diabody showing binding to Aβ and C1q. Phase I, diabody binding to immobilized Aβ chip. Phase II, C1q binding to Aβ/diabody complex.

A biosensor sandwich assay utilizing immobilized Aβ on the biosensor chip surface was used to demonstrate that both Aβ and C1q binding activities were present. After addition of the purified diabody sample, the signal increased by around 100 RU as expected due to binding of the diabody to Aβ (FIG. 3, phase 1). After a rinse step to dissociate non-specifically bound diabody, the second antigen, C1q, was injected over the chip surface, resulting in a further 200 RU increase in the observed signal corresponding to C1q binding to the diabody (FIG. 3 Phase 2). These results demonstrate that both binding activities are functional in the diabody construct.

Isolating Antibodies that Activate Microglial Cells.

While scFvs that activate leukocytes are available, the scFvs may not bind similar receptors microglial cells, which are much less well characterized. In order to ensure that the scFvs can directly activate microglial cells, a phage-display library is panned for members that activate microglial cells. There are two different approaches can be used to isolate scFvs that activate microglial cells: the first is similar to conventional biopanning using microtitre wells, the second is to use a cell sorting flow cytometer (FACS).

In the first approach, microglial cells are incubated with aliquots from the antibody library. Non-binding phage is eluted, and bound phage recovered by infection with *E. coli* as routinely done in other biopanning protocols. After several rounds of panning in this manner single antibody clones are assayed for microglial activation. Those clones that activate microglial cells are used in diabody constructs for ex-vivo Aβ targeting and clearance assays.

Alternatively, phage are identified that activate microglial cells by directly isolating activated microglial cells and recovering bound phage. FACS is used to sort out activated microglial cells containing phage displayed antibody bound to a cell receptor site. Specifically, the microglial cells are cultured with phage-displayed antibodies for various time periods, after which unbound phage is washed away. The cells are then be stained with fluorescence-labeled anti-phage antibody. Since the activated microglial cells are much bigger than resting cells, activated microglial cells can be isolated based on both fluorescence intensity and forward scatter/size scatter. Recovered scFv fragments are tested for ability to activate microglial cells, and then used for diabody constructs and ex-vivo assays.

Ex Vivo Aβ Clearance Assays Using Microglial Cells.

Since in vivo immunization studies are time consuming and expensive, an assay to select the most promising antibody constructs represent a valuable screening tool. An ex vivo assay for Aβ clearance has been shown to reliably predict results obtained in in vivo Aβ clearance studies (Bard et al. 2000). Since initiating the complement cascade requires binding of two adjacent Fc regions within 30-40 nm of each other, in certain embodiments two different scFv diabodies containing scFvs that recognize two different regions of the Aβ molecule are utilized. However, since Aβ can also bind C1q by itself, in certain embodiments a second binding site at the scFv is sufficient to initiate clearance. In certain embodiments, the scFv directed toward serum Ig initiates clearance of soluble Aβ alone since it is capable of binding IgM as well as IgG. Since only one molecule of IgM can multiply bind C1q, forming a stable complex, in certain embodiments, a single diabody targeting soluble Aβ and serum Ig initiates phagocytosis.

a) Isolation and Characterization of Microglia.

Microglial cells are obtained from mouse brain tissues and are prepared and isolated according to a previously described method (Lue et al. 1996). Briefly, frontal cortex samples are removed at autopsy under aseptic conditions, then quickly immersed in ice cold Hank's balanced salt solution (HBSS) (Irvine Scientific, CA). Enzymatic dissociation is processed as described elsewhere (Kim et al. 1983). Samples are washed with several changes of HBSS, after which all visible connective tissues and blood vessels are removed. The tissues are minced and incubated with a $Ca^{2+}$ and $Mg^{2+}$ free HBSS solution with 2.5% trypsin (Life Technologies, MD) and 2 mg/mL deoxyribonuclease I (Amersham, Ill.), then incubated in a shaking water bath at 37 C for 30 min. and 150 rpm. After the incubation, 2 mL of fetal bovine serum is added to stop the enzymatic digestion. The digested sample is triturated and centrifuged at 1500 rpm for 30 min. The pellets are resuspended in 40 mL HBSS and filtered through 130 μm, 100 μm and 200 μm mesh. The filtrate is subsequently spun at 15,000 rpm in 100% Percoll (Sigma) for 30 min at 3 C. The viable cell layer (middle layer) is transferred to 50 mL centrifuge tubes and washed twice with HBSS. A third wash is performed in growth medium consisting of DMEM (Life Technologies) with high glucose (25 mM), 2% HEPES, 1% sodium pyruvate, 10% fetal bovine serum (FBS), and 0.1% gentamicin (Sigma). After the third wash, cells are resuspended in growth medium and plated in 24 well plates (Corning, N.Y.) coated with poly-D-lysine (Sigma) at a density of about $1.0 \times 10^6$ cells per well. Cells are incubated with the growth medium at 37 C in 5% $CO_2$ for 18-24 hours when microglia cells will adhere to the culture ware surfaces. The non-adherent astrocytes are removed. The microglial cells are then cultured in the growth medium with weekly medium change, and cells are used two weeks after the initial plating for studies.

b) Immunofluorescence Phagocytosis Assay with Treatments of Bispecific Antibodies.

Microglia phagocytic activity is quantified by measuring the fluorescence of the fluo-Aβ42 (both freshly made and aggregated form) or fluorescein-labeled *Escherichia coli* K-12 BioParticles (fluo-*E. coli*) (Molecular Probe, Eugene, Oreg.) that are internalized. Cells are cultured in 24 well plates. To determine general phagocytic activity using various concentrations of the bispecific antibodies (10 ng/ml, 25 ng/ml, 50 ng/ml, 100 ng/ml 200 ng/ml, 400 ng/ml and 800 ng/ml) against monomer or oligomer and fibril Aβ treatments, cells are incubated with fluo-*E. coli* for 2 hours at room temperature. Trypan Blue is added immediately after removing the fluo-*E. coli* from cells to quench the extracellular probe. The wells of the plate are read by the Wallac Victor2 1420 multilabel counter (Wallac, Md.) using 480 nm excitation, 520 nm emission. Data is analyzed using Wallac Explore. For measuring the effect of aggregation of Aβ, the fluo-Aβ is dissolved in DMSO then diluted in serum free culture medium, and allowed to aggregate for 1 hour at room temperature. The aggregated Aβ is vortexed, and sonicated before being added to microglial cultures. The conditioned medium and cell lysate are measured by the Wallac Victor2 1420 multilabel counter.

c) Immunocytochemistry.

Immunocytochemistry of microglial cells is performed with polyclonal antibody Fc receptor gamma, and polyclonal MHCII. Cells are fixed with 4% paraformaldehyde for 15 min. at room temperature, washed with PBS three times, and then blocked with blocking buffer (2% BSA, 2% goat serum and 0.05% Triton X-100 in PBS) for 30 min. at room temperature. Cells are incubated with primary antibody for three days at 4° C. Then cells are rinsed with PBS three times and incubated with secondary antibodies (Santa Cruz, Calif.) for 1 hour at room temperature. To verify the internalization of Aβ by microglia, two sets of cells are incubated with unlabeled Aβ42 (Bachem, Calif.). Before blotting the cells with the anti-Aβ antibody (1:500 dilution, N-terminal 16-24) (Senetek, N.Y.), one set of cells is permeabilized with 0.1% Triton X-100 and the other without. A fluorescence microscope (Leica, Germany) with 25× and 100× objective will be used to observe a large number of cells per field.

In Vivo Assay Using APP23 Transgenic Mice:

In Vivo Assays: Tests are performed to determine whether diabodies directed at clearing specific morphologies of Aβ can reduce amyloidogenic APP processing in transgenic mouse models of AD. As an in vivo validation of the efficacy of the diabody constructs in clearing Aβ and preventing plaque deposition, the diabodies are administered intraperitoneally in transgenic mouse models of AD. The in vivo efficacy of administering the Aβ clearing diabodies as a means to reduce Aβ toxicity using similar methodologies is further tested. Five PSAPP/group mice are chosen in gender matched groups for each treatment arm. Beginning at 8 weeks of age, PSAPP mice are i.p. injected with 100 μg of the appropriate diabody once every ten days for periods of 1, 2, and 3 months. Initial test doses of these diabodies (1 μg to 1 mg) are tried in PSAPP mice to ensure that antibody penetration of the BBB occurs. Mouse brain is stained using a labeled anti-myc antibody such as 9E10 to detect penetration of i.p. injected diabody. The mice are sacrificed at 3 months of age for analysis of pathology. A control diabody with no activity to Aβ or clearance mechanisms is also be administered. The effect of the diabodies on APP processing is assessed by monitoring the extent of plaque deposition in the brain and the levels of the various APP proteolytic products, including Aβ, C99, and C83.

EXAMPLE 2

Aβ is proving to be a critical component in the etiology of AD. Accumulation of soluble Aβ has been correlated with the severity of AD and is thought to lead to diffuse plaque formation, setting off a cascade of events including activation of microglial cells and inflammation. The combination of these events is thought to lead to neural dysfunction, cell death and misprocessing of tau, resulting in the other dominant pathological feature of AD, neurofibrillary tangles. Furthermore, early-onset familial forms of AD are linked to mutations in the amyloid precursor protein and presenilin genes, which play central roles in the production and deposition of Aβ. Intermediate Aβ morphologies including small soluble oligomers and protofibrils have been implicated in AD. Soluble oligomers of Aβ were shown to be cytotoxic, disrupt neuronal functions including LTP and learning, and correlate better with progression of AD and have been identified in AD brains. Therefore well defined, highly specific reagents that can identify individual morphologies of Aβ are a valuable tool for studying and potentially treating AD. The inventors have developed a novel technology that utilizes AFM to identify specific protein morphologies and simultaneously isolate scFvs that bind the target morphology. In order to apply this technology to isolating scFvs against specific Aβ morphologies we first need to refine the panning protocols to favor selection for each of the various Aβ forms.

Inhibition of Aβ Aggregation with scFvs.

The inventors isolated scFvs to different regions of full length Aβ and demonstrated that the scFvs can successfully inhibit aggregation and toxicity of AP. The inventors characterized two scFvs against Aβ and defined their binding epitopes by immobilizing various Aβ peptides to a biosensor surface and testing for binding. It has been demonstrated that the scFvs could inhibit Aβ aggregation utilizing both Thioflavin fluorescence assays and AFM image analysis. It was showed that we could image various Aβ morphologies by AFM, and that we could quantify the distribution of oligomeric aggregate sizes. It was also demonstrated that toxic effects of Aβ aggregation on the neuroblastoma cell line, SH-SY5Y could be alleviated by incubation with scFvs.

It was further identified that critical regions of Aβ that control the aggregation state of the protein. We incubated various peptide fragments of Aβ both alone and in conjunction with Aβ and showed that residues 17-20 and 30-35 play essential roles in the aggregation process. In addition, we showed that the 25-35 peptide, previously shown to be highly toxic to cells, promotes formation of oligomers and protofibrils in Aβ42, but not fibrils, and the peptide by itself forms small oligomeric structures and very thin, long filaments. These results prompted the inventors to isolate scFvs to the 25-35 region of Aβ to test how they alter aggregation and toxicity. It was shown that scFvs generated against this region are very effective at reducing both aggregation and cytotoxicity (Zameer et al. 2006).

Affinity Maturation of Antibodies to Aβ.

Figure 4:
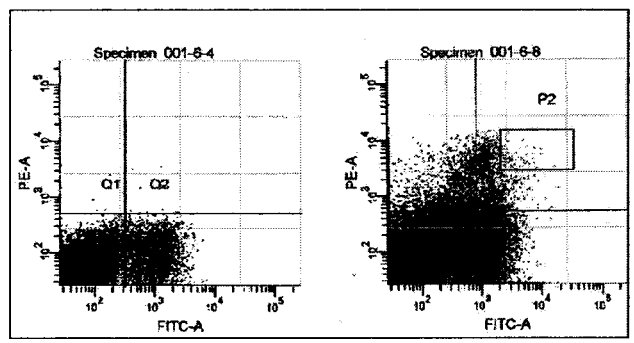
FIG. 4. Sorting of p6 peptide, left: no antigen; right: 100 nM antigen. Cells in quadrant 2 should bind target antigen. Boxed area shows selection criteria for sorted cells.

The inventors identified a scFv with the modest affinity for Aβ (high nanomolar affinity), H1 (see FIG. 7), and used this scFv as a parent sequence for affinity maturation studies to generate scFvs with increased affinity for Aβ. The inventors have successfully increased the affinity of the parent H1 scFv approximately 5-fold ($K_D$ of H1v2=2.47×10-7 M) through standard affinity maturation protocols (Schier et al. 1996). The inventors have developed a modified protocol using a BIACore biosensor to directly select for scFvs with slower off-rates, and have isolated scFvs with 10-fold better $K_D$ values than the H1v2 clone isolated from the same library using the standard protocol (Yuan et al. 2006). The inventors have also utilized the yeast display library to isolate scFvs against biotinylated peptides at their N-terminal of α-synuclein, experiments that are essentially identical to those that can be performed for affinity maturation studies. After four rounds of magnetic bead enrichment and FACS sorting as described in the methods section, over 10% of the cells show positive binding as shown with one of the target antigens (FIG. 4).

Isolating Morphology Specific ScFvs.

Figure 5:
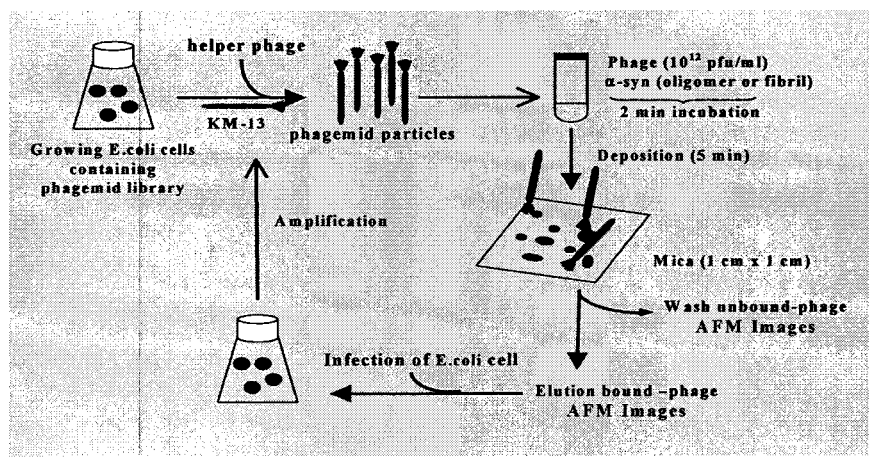
FIG. 5. Schematic of Atomic Force Microscope (AFM) biopanning protocol.

An increasing number of studies suggest that a number of different neurological diseases, i.e. AD, PD, Huntington and ALS, share a common pathological mechanism, namely, a misfolded protein that aggregates and leads to a dysfunction in the central nervous system (Forman et al. 2004)). The proteins accumulate as fibrillar β-pleated sheet structures in specific regions and cells of the brain depending on the protein and disease involved. All the proteins appear to follow similar pathways in the aggregation process, first increasing β-sheet content, then forming small oligomers and protofibrils intermediates, and finally forming fibrillar amyloid deposits. In order to define the role of these intermediates in the various diseases, it would be extremely beneficial to have highly specific reagents to identify the different protein forms. Toward this goal, the inventors have developed a biopanning technology to enable the isolation of scFvs that bind specific morphologies. The inventors have combined the imaging capabilities of AFM with phage display antibody technology to allow the identification of the presence of a specific protein morphology and then isolate scFvs that bind that morphology (Barkhordarian et al. 2006). The basic protocol is illustrated in FIG. 5.

To demonstrate the capabilities of this technology, scFvs were isolated that bind either oligomeric or fibrillar morphologies of α-synuclein and Aβ. First, incubation conditions were identified that favor formation of either oligomers or fibrils. To verify the protein morphology, an aliquot (10 μl) of the incubated solution was deposited on freshly cleaved mica and fixed for 5 minutes. Then the substrate was washed three times with 1 ml of ultra-pure water. The sample was then dried under a gentle stream of argon gas and imaged by AFM. Using this protocol the inventors were able to reliably reproduce oligomeric and fibrillar samples (see FIGS. 6A and 6B).

Figures 6A, 6B:
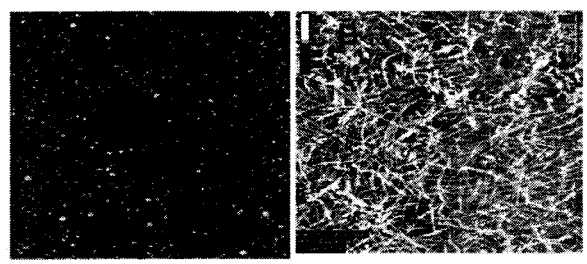
FIGS. 6A and 6B. The AFM image of formation of oligomeric (A) and fibrillar α-synuclein aggregates (B). The sample of monomeric or a mixture of monomer and oligomeric α-synuclein were dissolved to a final concentration of 70 μM. To form fibrils, the sample was incubated at 56° C. for 12 days and then at 37° C. for 7 days without shaking and finally incubated at 4° C. for 10 more days.

Utilizing the novel AFM biopanning technology (see FIG. 5), the inventors isolated scFvs against fibrillar (Barkhordarian et al. 2006) and oligomeric a-syn (Emadi et al. 2007) forms. For both panning cases, after only two rounds of biopanning, around 50% of recovered clones indicated positive binding to the desired target in a preliminary ELISA test. One of the stronger binding clones was selected based on the preliminary test and showed that the anti-oligomeric a-syn scFv specifically bound only an oligomeric form of a-syn, and not monomeric or fibrillar forms. We also showed that the anti-oligomer scFv could inhibit formation of fibrils, but not oligomers, that oligomeric, but not monomeric or fibrillar a-syn when added extracellularly to a neuronal cell line exhibited cytotoxicity, and that the anti-oligomeric scFv could inhibit toxicity of preformed a-syn oligomers (Emadi et al. 2007). We have also isolated a second scFv against a larger oligomeric form of a-syn. The two different anti-oligomeric scFvs do not show cross reactivity, the scFv binding the smaller earlier stage oligomers does not react with larger later stage oligomers, and the scFv against larger later stage a-syn oligomers does not react with the smaller, earlier stage oligomers (FIGS. 6A and 6B). In addition the anti-syn oligomeric scFvs do not cross react with Aβ oligomers. Significantly, both the anti-syn oligomer scFvs recognized aggregates in human tissue samples taken from Parkinson's brains, but not from Alzheimer's or control brain.

The inventors have also isolated an scFv against oligomeric Aβ. The scFv recognizes a larger later stage oligomeric form of Aβ. The scFvs against oligomeric Aβ did not cross react with a-syn oligomers and also labeled samples taken from human AD brain tissue, but not Parkinson's brain or control brain tissue. The anti-oligomeric Aβ scFv also inhibited aggregation and toxicity of Aβ towards SH-SY5Y cells (Zameer et al. 2008).

Aβ Aggregation.

Soluble oligomers of Aβ are formed as transient intermediates during the aggregation of monomeric Aβ to fibrillar amyloid. In order to reproducibly form Aβ aggregate morphologies, it is critical to remove any preformed Aβ aggregate seeds. The inventors dissolve lyophilized Aβ in hexafluoroisopropanol (HFIP), centrifuge, aliquot into Eppendorf tubes and then dry with nitrogen as described (Liu et al. 2004; Liu et al. 2005) to prepare standard monomeric Aβ stock solutions. Aβ oligomers can be formed by dissolving the Aβ stock solutions in solution with DMSO and diluting in buffer as described (Liu et al. 2004; Liu et al. 2004) or dissolving in HFIP and diluting (Kayed et al. 2003; Stine et al. 2003). Increasing concentrations of Aβ form fibrillar aggregates more quickly, while increasing concentrations of DMSO will decrease the aggregation rate.

AFM Imaging.

AFM images surfaces by scanning them in a raster pattern with a fine tip. The AFM tip follows the contour of surface structure which is then depicted on a computer screen directly during scanning. The inventors have found that deposition of the aggregate samples on unmodified freshly cleaved mica allows the ability to obtain high quality images of the protein aggregates. The main advantage of using bare mica however is that phage particles do not bind to this surface well, and unbound phage can be readily washed off as described in the preliminary results section.

Phage Preparation.

The Tomlinson I and J scFv libraries supplied by the Cambridge Antibody Technology (Cambridge, England) are used for phage preparation. Both libraries (I and J) are based on a single human framework for VH and VL and use pIT2 as a phagemid vector. The CDR3 of the heavy chain was designed to be as short as possible yet still allow for antigen binding. Side-chain diversity was incorporated in CDR3 and CDR2 regions at positions which make contacts to the antigens and are highly diverse in their mature native repertoire. CDR1 regions are kept constant. The size of each library is about $1.4 \times 10^8$. The libraries contain clones that were pre-selected for active folding domains by binding to Protein-L and Protein-A. Both libraries are grown separately, and their phage mixed 1:1 for selection protocols. Phage is produced from the initial bacterial library stock by superinfection of the bacterial culture with helper phage KM13 as described by CAT. Phage samples are purified from the supernatant by polyethylene glycol (PEG) precipitation and resuspended in PBS (phosphate-buffered saline) and used for panning.

AFM Panning and Selection.

The AFM biopanning and selection protocols to isolate scFvs against specific morphologies of a-syn and are performed essentially as described (Barkhordarian et al. 2006; Emadi et al. 2007; Zameer et al. 2008).

Binding Kinetics.

Antibody binding studies are performed by surface plasmon resonance using a BIAcore X biosensor. Surface plasmon resonance is based on the principle that light waves at a metal surface can be resonantly coupled into electric oscillations, or surface plasmons. The surface plasmons generate an evanescent wave that decays with increasing distance from the metal surface. Protein interactions at the surface alter the evanescent wave and plasmon characteristics, changing the internally reflected light signal. This change in reflected light can be quantitatively monitored using a diode array. To test for binding affinities to the various Aβ morphologies, the different scFvs are individually immobilized on carboxymethyl dextran sensor chips (CM5, Biosensor) by amine coupling. The dextran surface of the sensor chip is first activated to produce N-hydroxysuccinimide esters using N-hydroxysuccinimide (NHS) and 1-ethyl-3-(3-diethylaminopropyl) Carbodiimide (EDC) (O'Shannessy et al. 1992). The scFv is then immobilized to the activated surface through primary amine groups. A solution containing one of the different Aβ morphologies is injected over the peptide surface at a rate of 5 μL/min. Bound Aβ is then allowed to dissociate completely by flowing buffer (PBS with 0.005% Tween) over the surface before the next sample is injected. The two rate constants, $k_{on}$ and $k_{off}$, and the corresponding equilibrium dissociation constant, $K_d=k_{off}/k_{on}$, can be obtained by curve fitting of the obtained data. In this manner the affinity of each scFv for each morphology of Aβ or for any other protein aggregate morphology is accurately calculated. If the calculated dissociation constant for a particular antibody is not sufficiently high enough for in vivo studies, the affinity of the antibody is increased by generating a secondary antibody library and rescreened.

Aggregation Kinetics.

Aβ aggregation in the presence of the different scFvs is monitored by Thioflavin fluorescence and AFM analysis. Thioflavin fluorescence is useful for monitoring fibril formation while AFM studies can determine the extent of fibrillar and oligomeric aggregation. AFM analysis is performed to determine the size distribution of the aggregated particles as well as to characterize antibody specificity.

Cytoxicity Assay.

Cell toxicity of the various aggregate samples with and without added scFv is tested using two different toxicity assays, reduction in mitochondrial activity using an MTT assay, and increase in released lactate dehyrogenase activity using an LDH assay. These assays have been previously described (Emadi et al. 2004; Liu et al. 2004; Liu et al. 2004; Liu et al. 2005; Zameer et al. 2006; Emadi et al. 2007; Nannenga et al. 2008; Zameer et al. 2008).

Affinity Maturation.

Phage Libraries: Antibodies with picomolar affinities for the different Aβ morphologies are sufficiently specific for use either as a diagnostic for detecting the presence of the individual morphologies in AD samples or as a potential therapeutic for targeting specific Aβ morphologies in vivo. Aβ is normally present in CSF at low nanomolar concentrations, so an antibody with picomolar affinity should readily bind a sufficient amount of soluble Aβ at normal levels. While it is not known what the concentration of oligomeric forms of Aβ are in vivo, the scFvs can be affinity matured to higher affinity if necessary. Antibodies with nanomolar affinities toward fibrillar Aβ were shown to successfully initiate antibody mediated clearance of Aβ deposits (Bard et al. 2000). To generate antibodies with picomolar affinity, in certain embodiments affinity maturation techniques may be utilized. A CDR region of each of the antibody light chain and heavy chain fragments is separately randomized and the chains are randomly shuffled and recombined to generate a secondary library of antibodies where the entire library is now based on antibody sequences specific for Aβ. The first generation of this library is constructed by randomizing the CDR3 region of the light chain essentially as described (Schier et al. 1996). The best binders from this new library is selected by panning as described above. Those scFvs with the highest affinity serve as the framework for the second generation library formed by randomizing the CDR2 regions of the heavy and light chain genes again essentially as described (Schier et al. 1996) and shuffling the light and heavy chains. The best binders from this second generation library are isolated and serve as the framework for the third generation library formed by randomizing the CDR1 regions of the light and heavy chains. With each generation scFvs are isolated with better and better affinity for Aβ. This type of affinity maturation is continued until scFvs with picomolar affinity for the different morphologies of Aβ are isolated. Affinity maturation of phage display peptides has routinely improved the affinity of the parent antibody (Jackson et al. 1995; Irving et al. 1996; Schier et al. 1996; Wu et al. 1998; Chowdhury and Pastan 1999; Olsen et al. 2000), even into the femtomolar range (Boder et al. 2000).

In addition, in certain embodiments, affinity mature scFvs are developed so that they bind not just a specific morphology, but a specific morphology of a specific protein. Current oligomeric antibodies recognize oligomeric structures of many different proteins (Kayed et al. 2003). While there are some advantages to such an antibody, there are also disadvantages in that these antibodies cannot distinguish the presence of insulin, Aβ, or synulein oligomers. With the present AFM panning protocol it is possible to select scFvs for a specific protein morphology form by using a two-step negative/positive selection. For example, one can generate a secondary library of scFvs against oligomeric Aβ. Using this secondary library, one can then pan for scFvs that are specific only for Aβ oligomers by modifying the panning protocol. One first performs a negative panning step by incubating the scFv library with the non-desired oligomeric proteins, (for example; synuclein, huntingtin, prion) to remove scFvs that recognize these aggregates. One then perform the positive panning step by taking the remaining non-bound phage and select for those that bind Aβ oligomers. The inventors have successfully utilized this two-step panning protocol to isolate scFvs to a specific protein among a family of related proteins (Wu et al. 1998).

Affinity maturation can be performed using phage display libraries or yeast display libraries. Each of these libraries has particular advantages for different situations. For oligomeric morphologies of Aβ where AFM must be used for the selection protocol, phage display libraries have to be used for the panning process. For monomeric or fibrillar morphologies where the protein can be tagged with biotin, yeast display libraries can be used. The advantage of yeast display libraries is that high affinity variants can be directly selected during the flow cytometry sorting process. Therefore both of these affinity maturation protocols are described below.

Affinity maturation of phage display antibodies has routinely improved the affinity of the parent, even evolving to obtain femtomolar affinity. The protocols for generating these second generation antibody libraries are described in the various references (Jackson et al. 1995; Irving et al. 1996; Schier et al. 1996; Wu et al. 1998; Chowdhury and Pastan 1999; Olsen et al. 2000). Basically, a second generation library will be constructed essentially as described (Kim and Tanzi 1997) with some minor modifications as follows. The CDR3 light chain region of the parent H1 scFv is randomized using a two-step PCR protocol. The scFv gene is amplified in the first PCR using the two primers: LMB3 (5'-CAG GAA ACA GCT ATG AC-3' (SEQ ID NO: 3)) and CDR3-6-VL-FOR (5'-CTT GGT CCC TCC GCC GAA TAC CAC NNN NNN NNN NNN NNN NNN AGA GGA GTT ACA GTA ATA GTC AGC CTC-3' (SEQ ID NO: 4)) where N represents a random nucleotide. The resulting PCR product has an Nco I restriction endonuclease site at the 5' end. In the second PCR step, the randomized CDR3 light chain fragments are further amplified using the following two primers: LMB3 (5'-CAG GAA ACA GCT ATG AC-3' (SEQ ID NO: 3)) and JL-NOT-FOR (5'-ATT GCT TTT CCT TTT TGC GGC CGC GCC TAG GAC GGT CAG CTT GGT CCC TCC GCC-3' (SEQ ID NO: 5)) to introduce a Not I restriction endonuclease site at the 3' end. The PCR product obtained after the two PCR steps is digested with both Nco I and Not I, and ligated into plasmid pHEN2, which is previously digested with Not I and Nco I. The ligated mixture is transformed into electrocompetent E. coli TG1 cells by electroporation to yield the second-generation phage display library. The second generation library is then utilized in biopanning experiments as described above. Additional library generation can be constructed by varying different CDR regions. While the primers will vary to flank the target CDR sequence, the protocols are essentially the same.

Affinity Maturation with Yeast Libraries.

Yeast surface display of scFv antibodies can also be used to isolate higher affinity clones from small (~1×10$^6$) mutagenic libraries generated from a unique antigen binding scFv clone (Boder et al. 2000). The secondary mutagenic libraries are constructed by amplifying the parental scFv gene using error-prone PCR to incorporate 3 to 7 point mutations/scFv (Stemmer 1994; Daugherty et al. 2000). The material is cloned into the surface expression vector using the endogenous homologous recombination system present in yeast, known as "Gap-Repair" (On-Weaver and Szostak 1983). Gap repair is an endogenous homologous recombination system in *S. cerevisiae* that allows gene insertion in chromosomes or plasmids at exact sites by utilizing as little as 30 base pair regions of homology between the gene of interest and its target site. This allows mutated libraries of 1-10×10$^6$ clones to be rapidly generated and screened by selecting the brightest antigen binding fraction of the sorted cell population using decreasing amounts of antigen relative to the KD of the starting parental clone. The screening involves 3 to 4 rounds of flow cytometry sorting as described above. Flow cytometry will either be performed at the shared user facility to be housed in the BIO-Design facility at ASU or through the continuing collaborative arrangement with Barrow's Neurological Institute where all of the preliminary data was obtained.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (L e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

CITATIONS

Akiyama H, Barger S, Barnum S, Bradt B, Bauer J, Cole G M, Cooper N R, Eikelenboom P, Emmerling M, Fiebich B L, Finch C E, Frautschy S, Griffin W S, Hampel H, Hull M, Landreth G, Lue L, Mrak R, Mackenzie I R, McGeer P L, O'Banion M K, Pachter J, Pasinetti G, Plata-Salaman C, Rogers J, Rydel R, Shen Y, Streit W, Strohmeyer R, Tooyoma I, Van Muiswinkel F L, Veerhuis R, Walker D, Webster S, Wegrzyniak B, Wenk G, Wyss-Coray T (2000) Inflammation and Alzheimer's disease. Neurobiol Aging 21:383-421.

Bard F, Cannon C, Barbour R, Burke R L, Games D, Grajeda H, Guido T, Hu K, Huang J, Johnson-Wood K, Khan K, Kholodenko D, Lee M, Lieberburg I, Motter R, Nguyen M, Soriano F, Vasquez N, Weiss K, Welch B, Seubert P, Schenk D, Yednock T (2000) Peripherally administered antibodies against amyloid beta-peptide enter the central nervous system and reduce pathology in a mouse model of Alzheimer disease. Nat Med 6:916-919.

Barkhordarian H, Emadi S, Schulz P, Sierks M R (2006) Isolating recombinant antibodies against specific protein morphologies using atomic force microscopy and phage display technologies. Protein Eng Des Sel 19:497-502.

Boder E T, Midelfort K S, Wittrup K D (2000) Directed evolution of antibody fragments with monovalent femtomolar antigen-binding affinity. Proc Natl Acad Sci USA 97:10701-10705.

Check E (2002) Nerve inflammation halts trial for Alzheimer's drug. Nature 415:462.

Chowdhury P S, Pastan I (1999) Improving antibody affinity by mimicking somatic hypermutation in vitro. Nat Biotechnol 17:568-572.

Curnow R T (1997) Clinical experience with CD64-directed immunotherapy. An overview. Cancer Immunol Immunother 45:210-215.

Daugherty P S, Chen G, Iverson B L, Georgiou G (2000) Quantitative analysis of the effect of the mutation frequency on the affinity maturation of single chain Fv antibodies. Proc Natl Acad Sci USA 97:2029-2034.

Emadi S, Barkhordarian H, Wang M S, Schulz P, Sierks M R (2007) Isolation of a human single chain antibody fragment against oligomeric alpha-synuclein that inhibits aggregation and prevents alpha-synuclein-induced toxicity. J Mol Biol 368:1132-1144.

Emadi S, Liu R, Yuan B, Schulz P, McAllister C, Lyubchenko Y, Messer A, Sierks M R (2004) Inhibiting aggregation of alpha-synuclein with human single chain antibody fragments. Biochemistry 43:2871-2878.

Forman M S, Trojanowski J Q, Lee V M (2004) Neurodegenerative diseases: a decade of discoveries paves the way for therapeutic breakthroughs. Nat Med 10:1055-1063.

Irving R A, Kortt A A, Hudson P J (1996) Affinity maturation of recombinant antibodies using *E. coli* mutator cells. Immunotechnology 2:127-143.

Jackson J R, Sathe G, Rosenberg M, Sweet R (1995) In vitro antibody maturation. Improvement of a high affinity, neutralizing antibody against IL-1 beta. J Immunol 154:3310-3319.

Kayed R, Head E, Thompson J L, McIntire T M, Milton S C, Cotman C W, Glabe C G (2003) Common structure of soluble amyloid oligomers implies common mechanism of pathogenesis. Science 300:486-489.

Kim S U, Sato Y, Silberberg D H, Pleasure D E, Rorke L B (1983) Long-term culture of human oligodendrocytes. Isolation, growth and identification. J Neurol Sci 62:295-301.

Kim T W, Tanzi R E (1997) Presenilins and Alzheimer's disease. Curr Opin Neurobiol 7:683-688.

Liu R, McAllister C, Lyubchenko Y, Sierks M R (2004a) Proteolytic antibody light chains alter beta-amyloid aggregation and prevent cytotoxicity. Biochemistry 43:9999-10007.

Liu R, McAllister C, Lyubchenko Y, Sierks M R (2004b) Residues 17-20 and 30-35 of beta-amyloid play critical roles in aggregation. J Neurosci Res 75:162-171.

Liu R, Barkhordarian H, Emadi S, Park C B, Sierks M R (2005) Trehalose differentially inhibits aggregation and neurotoxicity of beta-amyloid 40 and 42. Neurobiol Dis 20:74-81.

Liu R, Yuan B, Emadi S, Zameer A, Schulz P, McAllister C, Lyubchenko Y, Goud G, Sierks M R (2004c) Single chain variable fragments against beta-amyloid (Abeta) can inhibit Abeta aggregation and prevent abeta-induced neurotoxicity. Biochemistry 43:6959-6967.

Lue L F, Brachova L, Walker D G, Rogers J (1996) Characterization of glial cultures from rapid autopsies of Alzheimer's and control patients. Neurobiol Aging 17:421-429.

McCall A M, Adams G P, Amoroso A R, Nielsen U B, Zhang L, Horak E, Simmons H, Schier R, Marks J D, Weiner L M (1999) Isolation and characterization of an anti-CD16 single-chain Fv fragment and construction of an anti-HER2/neu/anti-CD16 bispecific scFv that triggers CD16-dependent tumor cytolysis. Mol Immunol 36:433-445.

Nannenga B L, Zameer A, Sierks M R (2008) Anti-oligomeric single chain variable domain antibody differentially affects huntingtin and alpha-synuclein aggregates. FEBS Lett 582:517-522.

Olsen M J, Stephens D, Griffiths D, Daugherty P, Georgiou G, Iverson B L (2000) Function-based isolation of novel enzymes from a large library. Nat Biotechnol 18:1071-1074.

Orr-Weaver T L, Szostak J W (1983) Yeast recombination: the association between double-strand gap repair and crossing-over. Proc Natl Acad Sci USA 80:4417-4421.

O'Shannessy D J, Brigham-Burke M, Peck K (1992) Immobilization chemistries suitable for use in the BIAcore surface plasmon resonance detector. Anal Biochem 205:132-136.

Schier R, McCall A, Adams G P, Marshall K W, Merritt H, Yim M, Crawford R S, Weiner L M, Marks C, Marks J D (1996) Isolation of picomolar affinity anti-c-erbB-2 single-chain Fv by molecular evolution of the complementarity determining regions in the center of the antibody binding site. J Mol Biol 263:551-567.

Shen Y, Meri S (2003) Yin and Yang: complement activation and regulation in Alzheimer's disease. Prog Neurobiol 70:463-472.

Stemmer W P (1994) Rapid evolution of a protein in vitro by DNA shuffling. Nature 370:389-391.

Stine W B, Jr., Dahlgren K N, Krafft G A, LaDu M J (2003) In vitro characterization of conditions for amyloid-beta peptide oligomerization and fibrillogenesis. J Biol Chem 278:11612-11622.

Wu H, Goud G N, Sierks M R (1998a) Artificial antibodies for affinity chromatography of homologous proteins: application to blood clotting proteins. Biotechnol Prog 14:496-499.

Wu H, Beuerlein G, Nie Y, Smith H, Lee B A, Hensler M, Huse W D, Watkins J D (1998b) Stepwise in vitro affinity maturation of Vitaxin, an alphav beta3-specific humanized mAb. Proc Natl Acad Sci USA 95:6037-6042.

Zameer A, Schulz P, Wang M S, Sierks M R (2006) Single chain Fv antibodies against the 25-35 Abeta fragment inhibit aggregation and toxicity of Abeta42. Biochemistry 45:11532-11539.

Zameer A, Kasturirangan S, Emadi S, Nimmagadda S V, Sierks M R (2008) Anti-oligomeric Abeta single-chain variable domain antibody blocks Abeta-induced toxicity against human neuroblastoma cells. J Mol Biol 384:917-928.

What is claimed is:

1. A bispecific antibody fragment comprising
   (a) a first scFv that is specific for soluble Aβ, wherein the first scFv is H1v2 anti-Ab40 (SEQ ID NO: 6), H1v3 anti-Ab40 (also called D9antiAb40) (SEQ ID NO: 7), or C1 antiAb40 (SEQ ID NO: 8), and
   (b) a second scFv that specifically activates a classical complement pathway component or directly activates microglial cells, wherein the scFv fragment specifically binds to C1q.

2. An antibody construct comprising the bispecific antibody fragment of claim 1, further comprising a second bispecific antibody fragment.

3. The bispecific antibody fragment of claim 1, further comprising a (Gly$_4$-Ser)$_3$ linker (SEQ ID NO: 1) operably linked between the first and second scFvs.

4. The bispecific antibody fragment of claim 3, further comprising a poly-His tail operably linked to either the first or second scFvs.

5. The bispecific antibody of claim 1, wherein
   (a) the first scFv is an H1 scFv specific for β-amyloid, wherein the first scFv has an amino-terminus and a carboxy-terminus, and
   (b) the second scFv is an scFv specific for C1q, wherein the second scFv has an amino-terminus and a carboxy-terminus, and wherein the bispecific antibody further comprises
   (c) a (Gly$_4$Ser)$_3$ peptide linker (SEQ ID NO: 1) operably linking the carboxy-terminus of the first scFv to the amino-terminus of the second scFv.

6. The bispecific antibody of claim 1, further comprising a gIII signal sequence operably linked to the amino-terminus of the first scFv.

7. The bispecific antibody of claim 1, further comprising a c-myc tag operably linked to the carboxy-terminus of the second scFv.

8. The bispecific antibody of claim 7, further comprising a (His)$_6$ tag (SEQ ID NO: 2) operably linked to the c-myc tag.

9. A nucleic acid encoding the bispecific antibody of claim 1.

10. An expression cassette comprising
    the nucleic acid sequence of claim 9, and
    a promoter.

11. A vector comprising the expression cassette of claim 10.

12. A cell comprising the nucleic acid of claim 9.

13. A therapeutic composition comprising the bispecific antibody of claim 1, in combination with a physiologically-acceptable, non-toxic vehicle.

14. A method of clearing aggregated and soluble Aβ comprising administering the bispecific antibody of claim 1.

15. The method of claim 14, wherein the aggregated and soluble Aβ is in a cell.

16. The method of claim 15 wherein aggregated and soluble Aβ is in brain tissue.

17. The method of claim 16, wherein the brain tissue is in a mammal.

* * * * *

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser Gly Gly Gly Ser Gly Gly Gly Gly Ser
1               5                   10                  15

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

-continued

<400> SEQUENCE: 2

His His His His His His
1               5

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caggaaacag ctatgac                                                 17

<210> SEQ ID NO 4
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(42)
<223> OTHER INFORMATION: a, c, t, g, unknown or other

<400> SEQUENCE: 4
cttggtccct ccgccgaata ccacnnnnnn nnnnnnnnnn nnagaggagt tacagtaata   60
gtcagcctc                                                          69

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
attgcttttc cttttgcgg ccgcgcctag gacggtcagc ttggtccctc cgcc          54

<210> SEQ ID NO 6
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Glu Val Gln Leu Val Glu Ser Gly Gly Gly Val Val Arg Pro
1               5                   10                  15

Gly Gly Ser Leu Arg Leu Ser Cys Ala Ala Ser Gly Phe Thr Phe Asp
            20                  25                  30

Asp Tyr Gly Met Ser Trp Val Arg Gln Ala Pro Gly Lys Gly Leu Glu
        35                  40                  45

Trp Val Ser Gly Ile Asn Trp Asn Gly Gly Ser Thr Gly Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Arg Arg Tyr Ala Leu Asp Tyr Trp Gly Gln Gly Thr
            100                 105                 110

Leu Val Thr Val Ser Arg Gly Gly Gly Ser Gly Gly Gly Gly Ser
        115                 120                 125

Gly Gly Gly Gly Ser Ser Glu Leu Thr Gln Asp Pro Ala Val Ser Val
        130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Gly

<210> SEQ ID NO 7
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Glu Val Gln Leu Val Glu Ser Gly Gly Val Val Arg Pro
1               5                   10                  15

Gly Gly Ser Leu Arg Leu Ser Cys Ala Ala Ser Gly Phe Thr Phe Asp
            20                  25                  30

Asp Tyr Gly Met Ser Trp Val Arg Gln Ala Pro Gly Lys Gly Leu Glu
        35                  40                  45

Trp Val Ser Gly Ile Asn Trp Asn Gly Gly Ser Thr Gly Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Arg Arg Tyr Ala Leu Asp Tyr Trp Gly Gln Gly Thr
            100                 105                 110

Leu Val Thr Val Ser Arg Gly Gly Gly Ser Gly Gly Gly Gly Ser
        115                 120                 125

Gly Gly Gly Gly Ser Ser Glu Leu Thr Gln Asp Pro Ala Val Ser Val
        130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

```
Ala Gln Ala Glu Asp Glu Ala Asp Tyr Tyr Cys Asn Ser Ser Gly Gly
        210                 215                 220

Val Met Ser Val Val Val Phe Gly Gly Gly Thr Lys Leu Thr Leu Leu
225                 230                 235                 240

Gly

<210> SEQ ID NO 8
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Gln Val Gln Leu Val Gln Ser Gly Ala Glu Val Lys Lys Thr
1               5                   10                  15

Gly Ser Ser Val Lys Val Ser Cys Lys Ala Ser Gly Tyr Thr Phe Thr
            20                  25                  30

Tyr Arg Tyr Leu His Trp Val Arg Gln Ala Pro Gly Gln Ala Leu Glu
        35                  40                  45

Trp Met Gly Trp Ile Thr Pro Phe Asn Gly Asn Thr Asn Tyr Ala Gln
    50                  55                  60

Lys Phe Gln Asp Arg Val Thr Ile Thr Arg Asp Arg Ser Met Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gln Lys Thr Arg Leu Phe Ser Ala Ile Met Pro Glu
            100                 105                 110

Trp Gly Gln Gly Thr Leu Val Thr Val Ser Arg Gly Gly Gly Gly Ser
        115                 120                 125

Gly Gly Gly Gly Ser Gly Gly Gly Ser Ser Glu Leu Thr Gln Asp
    130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Gln Ala Pro Val Leu Val Ile Tyr Gly Lys Asn Asn Arg Pro Ser
            180                 185                 190

Gly Ile Pro Asp Arg Phe Ser Gly Ser Ser Ser Gly Asn Thr Ala Ser
        195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Asn His Val Val Phe Gly Gly Gly Thr
225                 230                 235                 240

Lys Leu Thr Val Leu Gly
                245
```